US006984499B2

(12) United States Patent
Chen et al.

(10) Patent No.: US 6,984,499 B2
(45) Date of Patent: Jan. 10, 2006

(54) METHOD AND APPARATUS FOR CONCURRENTLY DETECTING PATHOGENIC ORGANISMS AND ANTIMICROBIAL SUSCEPTIBILITY

(75) Inventors: Chun-Ming Chen, Falmouth, ME (US); Charles R. Carpenter, Scarborough, ME (US); Haoyi Gu, Portland, ME (US); Ali Naqui, Falmouth, ME (US)

(73) Assignee: IDEXX Laboratories, Inc., Westbrook, ME (US)

( * ) Notice: Subject to any disclaimer, the term of this patent is extended or adjusted under 35 U.S.C. 154(b) by 643 days.

(21) Appl. No.: 08/942,369

(22) Filed: Oct. 2, 1997

(65) Prior Publication Data

US 2002/0076742 A1    Jun. 20, 2002

(51) Int. Cl.
*C12Q 1/04*      (2006.01)
*C12Q 1/18*      (2006.01)
(52) U.S. Cl. .......................................... 435/34; 435/32
(58) Field of Classification Search ................. 435/31, 435/34, 36, 253.6, 288.4, 32; 536/16.8; 514/192, 514/312
See application file for complete search history.

(56) References Cited

U.S. PATENT DOCUMENTS

| | | | | |
|---|---|---|---|---|
| 3,272,719 | A | * | 9/1966 | Avakian ...................... 435/30 |
| 3,509,026 | A | * | 4/1970 | Sanders ....................... 435/33 |
| 3,832,532 | A | | 8/1974 | Praglin et al. ........... 235/151.3 |
| 3,957,583 | A | * | 5/1976 | Gibson et al. ................ 435/33 |
| 4,046,138 | A | * | 9/1977 | Libman et al. ............. 128/2 F |
| 4,077,845 | A | * | 3/1978 | Johnson ....................... 435/33 |
| 4,236,211 | A | | 11/1980 | Arvesen ...................... 364/413 |
| 4,591,554 | A | | 5/1986 | Koumura et al. ............. 435/18 |
| 4,925,789 | A | * | 5/1990 | Edberg ......................... 435/38 |
| 5,064,756 | A | | 11/1991 | Carr et al. .................... 435/32 |
| 5,236,827 | A | | 8/1993 | Sussman et al. .............. 435/34 |
| 5,457,030 | A | | 10/1995 | Badal et al. .................. 435/34 |
| 5,578,604 | A | * | 11/1996 | Himmler et al. ............ 514/312 |
| 5,620,865 | A | | 4/1997 | Chen et al. ................... 435/34 |
| 5,650,290 | A | | 7/1997 | Grant | |
| 6,090,541 | A | | 7/2000 | Wicks et al. | |
| 6,251,624 | B1 | | 6/2001 | Matsumura et al. | |

FOREIGN PATENT DOCUMENTS

| | | | |
|---|---|---|---|
| GB | 2 128 737 A | | 5/1984 |
| JP | 04051890 | * | 2/1992 |
| WO | 92/19763 | | 11/1992 |
| WO | 94/16097 | | 7/1994 |
| WO | WO 94/16097 | * | 7/1994 |
| WO | 96/28570 | | 9/1996 |
| WO | 96/40981 | | 12/1996 |

OTHER PUBLICATIONS

The Manual of Clinical Microbiology, Lennette, E.H ed. American Society for Microbiology, Washington D.C. pp. 264-265, 1041, 1074. (1985).*
Thaller et al.," New Plate Medium for Screeining and Presumptive Identification of Gram-Negative Urinary Tract Pathogens", J. of Clinical Microbiology (1988) vol. 26 No. 4 pp. 791-793.*
Murray, et al., (eds), *Manual of Clinical Microbiology*, 6th ed. (1995) (Table of Contents), pp. v-ix.
Perry et al., "Umbelliferyl-Labeled Galactosaminide as an Aid in Identification of *Candida albicans,*" *J. Clin. Micro.* 25:2424-2425, Dec. 1987.
Staneck, et al., "Automated Reading of MIC Microdilution Trays Containing Fluorogenic Enzyme Substrates with the Sensititre Autoreader," *J. Clin. Microbiol.* 22:187-191, Aug. 1985.
Urban and Jarstrand, "Rapid Determination of the Susceptibility of Bacteria to Antibiotics with 'Sensititre' Plates and Nitroblue Tetrazolium," *J. Antimicro. Chem.* 8:363-369 (1981).
Williams and Wilkins, *Bergey's Manual of Systematic Bateriology* vol. 1 (1989) (Table of Contents), pp. xxiii-xxvii, vol. 2, pp. xxi-xxiii, vol. 3, pp. xxiii-xxviii, vol. 4, pp. xxi-xxii.
International Search Report for international application PCT/US03/00655 filed Jan. 9, 2003.

* cited by examiner

*Primary Examiner*—Marjorie A. Moran
(74) *Attorney, Agent, or Firm*—McDonnell Boehnen Hulbert & Berghoff LLP

(57) ABSTRACT

The present invention relates to a method of detecting the presence of target microorganisms in a biological sample and of simultaneously determining the susceptibility of the microorganisms to antimicrobial agents. The target microbial organisms may be urinary pathogens. The methods include the steps of providing a multicompartment assay device with at least one compartment containing a medium capable of sustaining the growth of total viable microorganisms, at least one compartment containing a medium capable of sustaining the growth of target microorganisms, and at least one compartment containing an antimicrobial susceptibility interpretation medium. A biological sample is placed in each compartment and the presence and antimicrobial susceptibility of the target microorganisms which may be present is determined by analyzing which compartments exhibit microbial growth.

19 Claims, No Drawings

METHOD AND APPARATUS FOR CONCURRENTLY DETECTING PATHOGENIC ORGANISMS AND ANTIMICROBIAL SUSCEPTIBILITY

FIELD OF THE INVENTION

This invention relates to the field of chemistry, biology, and microbiology. In particular, it relates to a microbiological test method, compositions and apparatus, and especially to microbial detection of the majority of gram negative urinary pathogens and to determining the antibiotic susceptibility of the urinary pathogens obtained directly from a urine sample.

BACKGROUND ART

Bacterial urinary tract infections are common human and veterinary diseases. The enteric gram negative bacilli normally reside in the intestinal tract and become pathogens when found in the urinary tract; these enteric bacilli are classified in the family of *Enterobacteriacae*. The primary causative agents of urinary tract infections are gram negative bacilli. Typically, these include *Escherichia coli, Klebsiella pneumoniae, Enterobacter cloacae*, and *Proteus mirabilis*, etc. Infrequently, gram positive cocci (such as, *Staphylococcus aureus* and *Enterococcus faecalis*) and other gram negative bacteria (such as, *Pseudomonas aeruginosa*) may be urinary pathogens. Other gram positive cocci (*Staphylococcus, Streptococcus*) and gram positive bacilli (diphtheriods, *Bacillus subtilis*) are most frequently encountered as normal urethral contaminants.

Bacteriologic testing is commonly performed on patients experiencing symptoms consistent with urinary tract infections. Microorganisms isolated from patients (human and veterinary) are tested to determine the identity of the pathogens and their susceptibility to antibiotics. Information pertaining to minimum inhibitory concentrations (MIC) or the categorical interpretations (susceptible, moderate susceptible, intermediate resistant, or resistant) of antimicrobial agents against an identified pathogen are critical for a (medical or veterinary) practitioner to confirm or select a proper treatment regime for urinary tract infections.

The clinical effectiveness of antimicrobial chemotherapy for bacterial urinary tract infections requires the correct identification of the causing pathogens and the selection of an appropriate antibiotic treatment regime to eradicate the disease-causing bacteria. The suspect pathogens are isolated by inoculating the specimen onto a culture medium, which is then incubated at 35° C. for 24–48 hours to obtain bacterial growth. The bacterial identity and its antimicrobial susceptibility are then determined by a series of subsequent biochemical tests and standard antimicrobial susceptibility tests.

Methods for routine antimicrobial susceptibility determination of the identified pathogens include the broth dilution method and the agar diffusion assay. The broth dilution method involves the inoculation of a standardized microbiological inoculum (e.g., $1-5 \times 10^5$ cfu/ml) of the pure bacterial isolate in question into a growth medium (typically, a cation-adjusted Mueller Hinton broth) containing a series of predetermined concentrations of a given antibiotic whose MIC is sought to be determined. The inoculated medium is incubated for 18–24 hours and observed for visible growth. The lowest antibiotic concentration that completely inhibits visible growth of the isolated organism as detected by the unaided eye is recorded as the MIC.

The agar diffusion method involves the placement of an antibiotic containing disc or an antibiotic gradient strip on the surface of an agar medium (typically Mueller Hinton agar plate) that has been inoculated with the pure isolate of the microorganism in question. The antibiotic substance then diffuses away from the disc such that the effective concentration of antibiotic varies as a function of the radius from the disc or strip. Thus, the diameter of a resulting no growth area about the disc should be proportional to the MIC.

Procedures to obtain these antibiotic susceptibility data are often time-consuming (48–72 hours), cumbersome, require highly skilled personnel, or require expensive, automatic equipment. Patients with symptoms of a urinary tract infection (in particular, feline and canine) are often treated without regard to bacteriologic finding because of time delays and cumbersome assay procedures required by conventional culture methods. This may compromise the quality of patient care and contribute to the emerging antibiotic resistant bacteria due to the improper use of antibiotics.

Thus, there is a need for improved microbiologic tests and antibiotic susceptibility tests, related materials, and related assay devices. If the test procedures could be simplified so that no highly skilled personnel were required for performing the test, and test results were obtained in a shorter period of time, it would facilitate the ability of health care practitioners to confirm or select a proper treatment regime for urinary tract infections. Earlier receipt by health care practitioners (medical or veterinary) of accurate antimicrobial susceptibility information would result in better patient care, and prevent the emerging of antibiotic resistant bacteria due to the improper use of antibiotics.

Furthermore, the use of chromogenic or fluorogenic enzyme substrates have been widely used in a varieties of microbial diagnostic applications. Edberg (U.S. Pat. No. 4,925,789) described a medium containing a nutrient indicator which, when metabolized by target bacteria, releases a moiety which imparts a color or other detectable change to the medium. Chen and Gu (U.S. Pat. No. 5,620,865) used a fluorogenic compound, 4-methylumbelliferyl-β-D-glucopyranoside, in a micro-specific medium for detecting enterococci. Townsend and Chen (U.S. application Ser. No. 08/484,593, filed Jun. 7, 1995) described the use of fluorogenic enzyme substrates cocktail to detect bacterial contamination in food products. Koumura et al. (U.S. Pat. No. 4,591,554) describes the use of 4-methylumbelliferyl derivatives fluorogenic analysis to detect and determine the number of microorganisms based on the amount of liberated umbelliferone derivatives. Perry and Miller used an umbelliferyl-conjugated N-acetyl-β-D-galctosaminide for specific identification of a pathogenic yeast, *Candida albicans*, (*J. Clin. Micro.* (1987) 25:2424–2425).

The traditional endpoint of antimicrobial susceptibility determination involves the direct visual or instrument recognition of microbial growth in either a biological matrix, e.g., broth or agar. Urban and Jarstrand used a nitroblue tetrazolium dye to determine the susceptibility of bacteria to antibiotics (*J. Antimicro. Chem.* (1981) 8:363–369). The SENSITITRE™ system uses an instrument capable of automatically reading antimicrobial susceptibility microdilution trays (*J. Clin. Microbiol.* (1985) 22:187–191). In this procedure, microbial growth and MIC are determined by the measurement of fluorescence produced by bacterial enzyme action on fluorescence substrates. It is disclosed that fluorogenic substrates for this group of bacteria are selected from 7-(N)-(aminoacyl)-7-amido-4-methylcoumarin, 4-methylumbellifery noanate, 4-methylumbelliferyl phosphate. Badal et al. (U.S. Pat. No. 5,457,030) disclosed the use of a mixture of fluorogenic substrates consisting of leucine-7-amido-4-methylcoumarin, phenylalanine-7-amido-4-methylcoumarin, and 4-methylumbelliferyl phosphate and a pre-determined amount of an antimicrobial agent to form a mixture to determine the antimicrobial susceptibility of the majority of clinically significant gram positive organisms.

All these prior art approaches involve the use of a clone of a bacterial isolate obtained from clinical specimen prior to identification and antimicrobial susceptibility tests. Colonies, i.e., clones, of bacterial cultures, when prepared from the biological specimen, are harvested after a sufficient period of growth. The harvested colony is suspended in a suitable aqueous liquid for biochemical identification and antimicrobial susceptibility test.

Although 90–95% of all urinary infections are caused by a single type of organism, contaminating normal flora are often present on the patient's skin or in the environment, and these organisms can provide an arbitrary contaminant to a urinary sample. Contaminating microflora in a urine specimen are particularly prevalent in veterinary practices relative to medical practice in humans; this is because the specimen collection in veterinary practices tends to be more difficult to control with animals. In general, feline and canine urine specimens may be obtained through a number of means including cystocentesis, catheterization, manual compression of the urinary bladder and natural micturition. Cystocentesis is least likely to introduce microscopic contaminants (including microbial contamination). If the samples are collected by manual compression of bladder or natural micturition, even with the effort of collecting "midstream" sample, microbial contamination in the sample is expected. Although cystocentesis is recommended, other methods are often used in veterinarian practices due to the difficulty in controlling animals. Problems with the contamination of urine specimens have, in the past, prevented accurate assessments of effective antibacterial therapies for urinary tract infections. Accordingly, devices and related methods are needed which distinguish uropathogens from contaminating organisms.

DISCLOSURE OF THE INVENTION

Disclosed is a multicompartment assay device comprising: at least one compartment comprising a viable organism control medium capable of sustaining growth of total microbial organisms; at least one compartment comprising a medium capable of selectively sustaining growth of target microbial organisms; and, at least one compartment comprising an antimicrobial susceptibility interpretation medium. The medium capable of sustaining growth of total microbial organisms can comprise a means for detection of total microbial organisms; the means for detection can comprise an enzyme substrate comprising a detectable moiety capable of being released from the substrate by action of a microbial enzyme. The medium capable of sustaining growth of target microbial organisms can comprise a means for detection of target microbial organisms; the means for detection of target microbial organisms can comprise an enzyme substrate comprising a detectable moiety capable of being released from the substrate by action of a microbial enzyme. The antimicrobial susceptibility interpretation medium can comprise a means for detection of microbial organisms which have grown or reproduced in the susceptibility interpretation medium; the means for detection can comprise an enzyme substrate comprising a detectable moiety capable of being released from the substrate by action of a microbial enzyme. The medium capable of sustaining growth of total microbial organisms, the medium capable of sustaining growth of target microbial organisms, and, the antimicrobial susceptibility interpretation medium each comprise a means for producing an identical type of detectable signal. The antimicrobial susceptibility interpretation medium can comprise amoxicillin, clavulanic acid/amoxicillin, or, enrofloxacin.

Disclosed is a method of detecting the presence of target microbial microorganisms in a biological sample and of simultaneously determining the susceptibility of such microorganisms to antimicrobial agents, said method comprising steps of: providing a multicompartment assay device comprising at least one compartment comprising a medium capable of sustaining growth of total microbial organisms, at least one compartment comprising a medium capable of sustaining growth of target microbial organisms; and, at least one compartment comprising an antimicrobial susceptibility interpretation medium; placing a portion of the biological sample respectively in said at least one compartment comprising a medium capable of sustaining growth of total microbial organisms; said at least one compartment comprising a medium capable of sustaining growth of target microbial organisms; and, said at least one compartment comprising an antimicrobial susceptibility interpretation medium comprising an antimicrobial agent; whereby growth of organisms in said at least one compartment comprising a medium capable of sustaining growth of total microbial organisms indicates the presence of bacteria in the sample; growth of organisms in said at least one compartment comprising a medium capable of sustaining growth of target microbial organisms indicates the presence of target microbial organisms in the sample, and growth of organisms in said at least one compartment comprising an antimicrobial susceptibility interpretation medium indicates that the organisms lack susceptibility to that antimicrobial agent. The biological fluid can be urine, blood, saliva, cerebrospinal fluid, fluid from a wound, a chemical sample, or an environmental sample. The target microbial microorganisms can be uropathogens, such as *Enterobacteriacae*; or, *Escherichia coli, Klebsiella* spp., *Enterobacter* spp., *Proteus mirabilis Proteus vulgaris, Morganella morganii, Providencia retteri, Acinetobacter* spp., *Staphylococcus aureus, Enterococcus faecalis*, or *Streptococci*.

The step of providing a device comprising the at least one antimicrobial susceptibility interpretation medium can provide an antimicrobial susceptibility interpretation medium comprising amoxicillin, clavulanic acid/amoxicillin, or, enrofloxacin.

Disclosed is a multicompartment assay device comprising: a compartment comprising a medium capable of sustaining growth of total bacterial organisms; a compartment comprising a medium capable of sustaining growth of target uropathogenic bacteria; a compartment comprising an antimicrobial susceptibility interpretation medium comprising amoxicillin; a compartment comprising an antimicrobial susceptibility interpretation medium comprising amoxicillin and clavulanic acid; and, a compartment comprising an antimicrobial susceptibility interpretation medium comprising enrofloxacin.

MODES FOR CARRYING OUT INVENTION

Definitions

The term "microbe" or "microbial organism" is intended any organism capable of being present in a biological sample. Such organisms include but are not limited to bacteria and fungi. Preferred embodiments of the invention detect bacterial microbes in a biological sample.

By "*Enterobacteriacae*" is meant the groups of gram negative rods, motile by perichichous flagella or nonmotile, which do not form endospores or microcysts, and, are not acid-fast. These group of bacteria can grow in the presence or absence of oxygen, use D-glucose as sole carbon source, and produce acid and visible gas. These include but are not limited to, the following genera of microorganisms: *Escherichia, Shigella, Klebsiella, Enterobacter, Citrobacter, Proteus, Salmonella, Providencia, Morganella, Yersinia, Erwinia,* and *Hafnia*. These bacteria include those described or referred to in "Bergey's Manual of Systematic Bacteriology" (1989) (Williams and Wilkins, U.S.A.).

By "urinary pathogen" or "uropathogen" is meant bacteria that cause the human and veterinary urinary tract infections. Such bacteria include, but are not limited to, the group of enteric gram negative bacilli (*Enterobacteriacae*) which normally reside in the intestinal tract, which when found in the urinary tract often produce clinical symptoms of urinary tract infection. Examples of these bacteria include but are not limited to, the enteric gram negative bacteria (such as *Escherichia coli, Klebsiella* spp., *Enterobacter* spp., *Proteus mirabilis, Proteus vulgaris, Morganella morganii, Providencia retteri,* and *Acinetobacter* spp.). Infrequently, *Pseudomonas* spp. and certain gram positive cocci (*Staphylococcus aureus, Enterococcus faecalis,* and *Streptococci*) may be urinary pathogens. These terms are not meant to exclude genera that have yet to be discovered but may later be identified and included in this group of bacteria by those skill in the art.

By a "primary gram negative urinary pathogens" is meant the group of bacteria which cause at least 85–90% of the human and veterinary urinary tract infections. These include but are not limited to: *Escherichia coli, Klebsiella* spp., *Enterobacter* spp., and *Proteus mirabilis*. This term is not meant to exclude genera that have yet to be discovered but may later be identified and included in this group of bacteria by those skill in the art.

By the term "target microbe" or "target microbial organism" means the microorganism whose presence or absence is sought to be detected. For example, it includes any species of the primary urinary pathogens or any microbe suspected of being present in a given biological sample.

By the term "viable organism control medium" means a medium which allows growth of total microbial organisms present in a test sample. For example, if fungi are detected, this medium is referred to as a "total viable fungi medium" or "TVF" medium, and is not selective for particular fungal species. If bacteria are detected, the media is referred to as "total viable bacteria medium" or "TVB medium", and includes any media which can support bacterial growth in a test sample, and is not selective for particular bacterial species; examples include but are not limited to, trypticase soy broth, nutrient broth, etc., as appreciated by one of ordinary skill in the art. In preferred embodiments, a "viable organism control medium" detects bacterial growth by providing the ability to identify bacterial enzymes (e.g., phosphatase, β-glucosidase, and L-alanine aminopeptidase) from diverse microbial species. In a preferred embodiment, the viable organism control medium is a medium described in the U.S. application Ser. No. 08/484,593, filed Jun. 7, 1995 in the names of Townsend and Chen, entitled, "Method and Composition for Detecting Bacterial Contamination in Food Products". In preferred embodiments, this term includes media which contain one or more enzyme substrates. The bacterial enzymes are identified because they liberate fluorescent moieties that exhibit detectable signals with identical emission wavelengths. This medium takes advantage of combining different bacterial enzyme activities from diverse microbes, to create a broader enzyme activity spectrum; the broadened spectrum enables the detection of total bacteria in a test sample. The microorganisms detected by this medium include but are not limited to the gram negative urinary pathogens (e.g., *Escherichia coli, Klebsiella* spp., *Enterobacter* spp., *Proteus mirabilis, Pseudomonas aeruginosa* etc.), the gram positive pathogens (*Staphylococcus aureus, Enterococci,* etc.), or other potentially contaminating microflora in the urine specimen.

By the term "target organism specific medium" is meant a medium capable of selectively sustaining the growth or ongoing viability of target microbial organisms. When the target organisms are uropathogenic bacteria, the "target organism specific medium" can be referred to as "uropathogen specific medium" or "UTI medium".

"Uropathogen specific medium" or "UTI medium" refer to a medium which allows only the growth of the primary urinary gram negative pathogens and allows for substantially less growth of any other bacteria of a biological matrix. In certain preferred embodiments, this term comprises media which contain one or more selecting compounds that are specific for inhibiting or preventing the growth of bacteria other than the primary gram negative urinary pathogens. In other preferred embodiments, it compromises media which contain one or more enzyme substrates which are preferably not hydrolyzed by enzymes from microorganisms other than the primary urinary gram negative pathogens to any substantial degree.

By the term "antimicrobial susceptibility interpretation medium" means a medium which allows the category of interpretation (e.g. susceptible, moderate susceptible, intermediate resistant, or resistant) of a detected target microbial organism relative to an antimicrobial agent or combinations thereof. These media are comprised of all components of the target organism specific media, such as the uropathogen specific medium, as well as a predetermined amount of an antimicrobial agent. For example, when the target microbial organisms are uropathogenic bacteria, the antimicrobial susceptibility interpretation medium detects the susceptibility of the target organisms toward an antibiotic; the antimicrobial susceptibility interpretation medium can detect antimicrobial efficacy of one or more antibiotics toward the primary gram negative urinary pathogens.

By "signal generating substrate" is meant a molecule which can be metabolized by an enzyme or a group of enzymes of the microorganisms whose presence or growth ability are sought to be detected. These include but are not limited to hydrolyzable enzyme substrates and redox dyes. The enzymatic reaction typically involves hydrolyzing one or more covalent bonds of the substrate or transferring the reducing equivalents from a specific substrate to an acceptor. The substrates typically contain detectable moieties or can be converted to a detectable compound. Upon being metabolized by one or more microbial enzymes, the substrate generates a detectable moiety in the medium. In the preferred embodiments, the signal generating substrate is selected from the chromogenic or fluorogenic substrates of phosphatase, aminopeptidases (e.g., L-alanine aminopeptidase or L-leucine aminopeptidase), glycosidases, esterases, and sulfatases, as well as from the chromogenic or fluorogenic tetrazolium compounds (such as, sodium 3'-{1-[(phenylamino)-carbonyl]-3,4-tetrazolium}bis(4-methoxy-6nitro) benzenesulfonic acid hydrate (XTT), 2-(p-iodophenyl)-3-(p-nitrophenyl)-5-phenyltetrazolium chloride (INT), 5-cyano-2,3-ditolyl tetrazolium chloride (CTC), 2,3,5-triphenyltetrazolium chloride (TTC), and resazurin, etc. This list is not meant to exclude signal generating substrates which have yet to be discovered but may later be identified and include in this list by those of ordinary skill in the art. In alternative preferred embodiments, signal generating substrates employed in the viable organism control medium are 4-methylumbellifery-phosphate, 4-methylumbellifery-β-D-glucoside, and L-alanine-7-amido-4-methylcoumarin. In further preferred embodiments, the signal generating substrate used in the uropathogen specific medium and in the antimicrobial susceptibility interpretation medium is 4-methylumbelliferyl-phosphate.

By "signal generating moiety" is meant a molecule or substance which can be affiliated with a nutrient moiety or exists as a separate discrete entity. The signal generating moiety does not cause or produce a detectable signal when it is affiliated with (e.g., covalently bonded to) the nutrient moiety or before reduced and metabolized by the organisms. However, when an enzyme or a group of enzymes from viable target bacteria metabolize the signal generating substrate, a signal generating moiety is released or formed and causes or is capable of producing a detectable signal in the medium. In preferred embodiments, the detectable moieties are fluorogens which produce and emit fluorescence when properly excited by an external energy source, or chromogens which preferably produce a color change observable in the visible wavelength range (alternatively in the ultraviolet or infrared spectra). Examples of signal generating moieties include, but are not limited to: 4-methylumbelliferone, orthonitrophenyl, para-nitrophenyl, para-nitoanilide, 4-methoxy-β-naphthylamide, 7-amido-4-chloro-3-indoxyl, and formazan, etc. In a further preferred embodiment, the signal generating moiety produce an identical type of detectable fluorescent signal upon release from a nutrient moiety and cause a change of fluorescence in the medium.

By "detectable signal" is meant a characteristic change in a medium or sample that is observable or measurable by physical, chemical, or biological means known to those skilled in the art. Such a detectable signal may be assayed by chemical, visual, tactile, or olfactory means. For example, a change in emission or absorbency of: visible or invisible light or radio waves at a certain wavelength, electrical conductivity, emission of gas, turbidity or odor. A detectable signal may also be a change in physical state such as between solid, liquid and gas. The detectable signal may produce a chemical change, such as change in pH, which is measurable. Typically, a detectable signal is measured visually; in preferred embodiments, detectable signals comprise a change in fluorescent or color emission of the medium.

By the term "inoculation" is meant the time at which the test sample is mixed with media of the invention.

By "multi-compartmentalized device" is meant a device which comprises a number of individual compartments By the term "effective amount of nutrients" is an amount of nutrients within the range which allows or promotes growth and reproduction of a target microorganism. That is, an amount which allows target microbes or other organisms to adapt to the media, continue metabolism, or synthesize the necessary constituents for reproduction and to subsequently reproduce.

By the term "effective amount of tested antibiotic" means an amount of an antibiotic within a range which is sufficient to impede or eliminate continued growth or reproduction of microbial organisms.

The terms "vitamins", "amino acids", "trace elements" and "salts" are meant to include all molecules, compounds, and substances (whether organic or inorganic) classified in each category by those of ordinary skill in the art. The combination of these categories in intended to include any substance which may be necessary for, or conductive to, maintaining life of microorganisms.

By "test sample" or "biological sample" is meant a fraction, aliquot, droplet, portion, or volume of a biological sample such as urine, blood, saliva, cerebro-spinal fluid, fluid from a wound, fluid or material from a sight of infection, or, a chemical or an environmental sample. The sample can be taken from a patient source such as a human, dog, cat, or horse, or any other source. A test sample may be taken from a source using techniques known to one skilled in the art, including but not limited to, those described or referred to in "Manual of Clinical Microbiology" (6th ed.) 1995. edited by P. R. Murray, E. J. Baron, M. A. Pfaller, F. C. Tenover, and R. H. Yolken.

In preferred embodiments, urine specimens may be obtained from cats or dogs suspected to have urinary tract infection by a number of means; including but are not limited to cystocentesis, catheterization, manual compression of bladder, and natural micturition.

MODES FOR CARRYING OUT THE INVENTION

The present invention comprises a device and procedure to determine the antibiotic susceptibility (e.g., susceptible, moderately susceptible, intermediate resistant, or resistant) of one or more antibiotics with respect to the urinary tract pathogens tested directly from a urine specimen. An aspect of the invention takes account of the interference caused by any contaminating microflora in the sample.

The present invention involves a microbiological method, compositions and apparatus for the direct detection and categorical interpretation of antibiotic susceptibility in relation to the majority of gram negative urinary tract pathogens directly from human or veterinary samples, such as urine or samples.

In preferred embodiments, a device in accordance with the invention comprises a series of wells, each well comprising an absorbent pad to which test media have been applied. Advantageously, the pad is capable of containing a liquid sample so that cross-contamination between wells is prevented, thus resulting in a reduced risk of erroneous results.

In alternative preferred embodiments, specific test media that have been applied to the well series of the test device include TVB medium, uropathogen specific medium, and a series of antimicrobial susceptibility interpretation media. The antimicrobial susceptibility interpretation media test series may be selected from, but are not limited to, the tests for the antimicrobial efficacy of amoxicillin, enrofloxacin, clavulanic acid/amoxicillin), cephalothin [cephalothin assay of often used to represent the efficacy of cephalothin, cephaprin, cephradine, cephalexin, cefaclor, and cefadroxil (NCCLS Antimicrobial Susceptibility Testing/SC3, January, 1996)], gentamicin, and chloramphenicol, etc. Preferably, the antimicrobial susceptibility interpretation media series for the primary urinary pathogens include tests for the efficacy of amoxicillin, enrofloxacin, clavulanic acid/amoxicillin, or cephalothin.

By the present invention, there is provided an improvement in the method of determining effective antibacterial therapy for human or veterinary urinary tract infections.

Preferably, the present invention combines a series of microbial culture media which allows detecting the primary urinary pathogens and determining the antibacterial efficacy of selected antibiotics towards the detected urinary pathogens in a single step, in which a urine specimen obtained from a patient suspected of having an infection (i.e. UTI) is added to a series of microbiological growth media containing one or more hydrolyzable fluorogenic or colorogenic signal generating substrates; the series of growth media include TVB medium, uropathogen specific medium, and antimicrobial susceptibility interpretation media series. These test materials and processes can, in certain cases also be arranged to allow conventional microbiological culture to be continued so that the exact identity of a pathogen and the quantitative antimicrobial susceptibility information obtained later as a confirmation if desired.

EXAMPLES

Example 1

This example illustrates the preparation of the UTI media for the urinary tract infection assay device.

The medium is formulated according to techniques well known to those skilled in the art. The UTI medium contains the following reagents in the concentration indicated in Table I.

TABLE I

|  | g/L |
| --- | --- |
| HEPES Free Acid | 6.864 |
| HEPES Sodium Salt | 5.292 |
| Modified Yeast Nitrogen Base* | 5.15 |
| Yeast Extract | 0.5 |
| Casein Peptone | 10 |
| Potassium Phosphate (monobasic) | 0.1 |
| Bile Salts #3 | 0.75 |
| Vancomycin | 0.01 |
| Amphotericin B | 0.0022 |
| Clindamycin-HCl | 0.005 |
| 4-MU Phosphate | 0.05 |

*Yeast nitrogen base without salts (potassium phosphate, magnesium sulfate, sodium chloride, calcium chloride)

A total of 303 feline and canine urine specimens collected from the animals suspected of having urinary tract infection were tested with the uropathogen specific medium. A 50 µl aliquot of the urine specimen was added to 10 ml of sterile saline solution (0.85% NaCl solution). A 100 µl of the diluted urine specimens was added to the uropathogen specific medium in the urinary tract infection device; the device was then incubated at 35° C. for 24 hours.

For comparison, a traditional microbiological culture and bacterial identification technique was used. A portion of 1 µl urine specimen was streaked onto a blood agar plate; the plate was then incubated at 35° C. for 24–48 hours. The positive cultures (plates that showed microbial growth) was then subcultured and subjected to biochemical identification to obtain the identity of the isolated culture.

Results of the experiment are summarized in Table II. These results indicated that the uropathogen specific medium has a positive predictive value of 94.8%, a negative predictive value of 99.2%, and an overall accuracy of 98.3%.

TABLE II

| Uropathogen Specific Medium | | | | |
| --- | --- | --- | --- | --- |
| | | Positive | Negative | Total |
| Conventional culture and identification | confirmed* | 55 | 2 | 57 |
| | Unconfirmed | 3 | 243 | 246 |
| | Total | 58 | 245 | 303 |

*The isolated culture was confirmed to be the primary urinary pathogens; such as *Escherichia coli*, *Kiebsiella pneumoniae*, *Enterobacter cloacae*, and *Proteus mirabilis*.

Example 2

This example illustrates the preparation of the antimicrobial susceptibility interpretation medium with amoxicillin for the urinary tract infection assay device.

The medium is formulated according to techniques well known to those skilled in the art. The medium comprises UTI media with amoxicillin at a concentration of 8 mg/liter.

A total of 303 feline and canine urine specimens were collected from the animals suspected of having urinary tract infection were tested with the "AMO" medium. A 50 µl aliquot of the urine specimen was added to 10 ml of sterile saline solution (0.85% NaCl solution). A 100 µl of the diluted urine specimens were added to the "AMO" medium in the urinary tract infection device; the device was then incubated at 35° C. for 24 hours.

For comparison a traditional microbiological culture, bacterial identification technique, and antimicrobial susceptibility test were performed. A portion of 1 µl urine specimen was streaked onto a blood agar plate; the plate was then incubated at 35° C. for 24–48 hours. The positive culture (plates that showed microbial growth) was then subcultured and subjected to biochemical identification to obtain the identity of the isolated culture. The susceptibility of amoxicillin of the gram negative urinary pathogens (*Escherichia coli*, *Klebsiella* spp, *Enterobacter* supp., and *Proteus* spp.) Were performed by standard Kirby-Bauer antimicrobial susceptibility assay.

Results of the experiment are summarized in Table III. These results indicated that AMO medium is equivalent to the conventional antimicrobial susceptibility test in predicting the *Klebsiella* spp, *Enterobacter* spp, and *Proteus* spp.). The statistical agreement between these two methods were 96.6%.

TABLE III

| AMO Medium | | | | |
| --- | --- | --- | --- | --- |
| | | Resistant | Susceptible | Total |
| Amoxicillin susceptibility (Kirby-Bauer Assay) | Resistant | 21 | 1 | 22 |
| | Susceptible | 1 | 35 | 36 |
| | Total | 22 | 36 | 58 |

*One urine specimen exhibited pseudofluorescence which resulted in a false prediction by AMO medium

Example 3

This example illustrates the preparation of the antimicrobial susceptibility interpretation media with amoxicillin/ clavulanic acid (AMC) (e.g., Clavamox®, Pfizer) for the urinary tract infection assay device.

The medium is formulated according to techniques well known to those skilled in the art. The medium comprises the UTI media with amoxicillin at a concentration of 12 mg/liter and clavulanic acid at a concentration of 6 mg/liter.

A total of 303 feline and canine urine specimens were collected from the animals suspected of having urinary tract infection were tested with the "AMC" medium. A 50 µl aliquot of the urine specimen was added to 10 ml of sterile saline solution (0.85% NaCl solution). A 100 µl of the diluted urine specimens was added to the "AMC" medium in the urinary tract infection device; the device was then incubated at 35° C. for 24 hours.

For comparison a traditional microbiological culture, bacterial identification technique, and antimicrobial susceptibility test were performed. A portion of 1 µl urine specimen was streaked onto a blood agar plate; the plate was then incubated at 35° C. for 24–48 hours. The positive culture (plates that showed microbial growth) was then subcultured and subjected to biochemical identification to obtain the identity of the isolated culture. The susceptibility of amoxicillin/clavulanic acid of the gram negative urinary pathogens (*Escherichia coli, Klebsiella* spp, *Enterobacter* spp., and *Proteus* spp.) Were preformed by standard Kirby-Bauer antimicrobial susceptibility assay.

Results of the experiment are summarized in Table IV. These results indicated that AMC medium is equivalent to the conventional antimicrobial susceptibility test in predicting the efficacy of amoxicillin/clavulanic acid in inhibiting the gram negative urinary pathogens (*Escherichia coli, Klebsiella* spp, *Enterobacter* spp., and *Proteus* spp.). The statistical agreement between these two methods were 91.4%.

TABLE IV

| AMC Medium | | | | |
|---|---|---|---|---|
| | | Resistant | Susceptible | Total |
| Amoxicillin/ clavulanic acid susceptibility (Kirby-Bauer Assay) | Resistant | 9 | 2 | 11 |
| | Susceptible | 3* | 44 | 47 |
| | Total | 12 | 46 | 58 |

*One urine specimen exhibited pseudofluorescence which resulted in a false prediction by AMC medium.

Example 4

This example illustrates the preparation of the antimicrobial susceptibility interpretation medium with enrofloxacin for the urinary tract infection assay device.

The medium is formulated according to techniques well known to those skilled in the art. The media comprises UTI media with enrofloxacin (ENR) at a concentration of 2.0 mg/liter.

A total of 303 feline and canine urine specimens were collected from the animals suspected of having urinary tract infection were tested with the "ENR" medium. A 50 µl aliquot of the urine specimen was added to 10 ml of sterile saline solution (0.85% NaCl solution). A 100 µl of the diluted urine specimens was added to the "ENR" medium in the urinary tract infection device; the device was then incubated at 35° C. for 24 hours.

For comparison a traditional microbiological culture, bacterial identification technique, and antimicrobial susceptibility test were performed. A portion of 1 µl urine specimen was streaked onto a blood agar plate; the plate was then incubated at 35° C. for 24–48 hours. The positive culture (plates that showed microbial growth) was then subcultured and subjected to biochemical identification to obtain the identity of the isolated culture. The susceptibility of enrofloxacin of the gram negative urinary pathogens (*Escherichia coli, Klebsiella* spp, *Enterobacter* spp., and *Proteus* spp.) were performed by standard Kirby-Bauer antimicrobial susceptibility assay.

Results of the experiment are summarized in Table V. These results indicated that AMC medium is equivalent to the conventional antimicrobial susceptibility test in predicting the efficacy of enrofloxacin in inhibiting the gram negative urinary pathogens (*Escherichia coli, Klebsiella* spp, *Enterobacter* spp, and *Proteus* spp.). The statistical agreement between these two methods were 94.8%.

TABLE V

| ENR Medium | | | | |
|---|---|---|---|---|
| | | Resistant | Susceptible | Total |
| Enrofloxacin Susceptibility (Kirby-Bauer Assay) | Resistant | 5 | 1 | 6 |
| | Susceptible | 2 | 50 | 52 |
| | Total | 7 | 51 | 58 |

*One urine specimen exhibited pseudofluorescence which resulted in a false prediction by AMC medium.

Example 5

This example illustrated the preparation of the antimicrobial susceptibility interpretation medium with cephalothin (CR30) for the urinary assay device.

The medium is formulated according to techniques well known to those skilled in the art. The medium comprises the uropathogen specific medium with 32 mg/liter of cephalothin.

The representative primary gram negative urinary pathogens including *Escherichia coli* ATCC 25922, *Klebsiella pneumoniae, Enterobacter cloacae* ATCC 13047, and *Proteus mirabilis* were used to determine the antimicrobial efficacy of cephalothin in CR 30 medium in reaction to the standard Muller Hinton microdilution antimicrobial susceptibility ((NCCLS Antimicrobial Susceptibility Testing/SC3, January, 1996). Cephalothin was prepared in both standard Muller Hinton broth (MHB) and CR30 medium (CR30M) at the following concentrations: 128, 64, 32, 16, 8, 4, 2, and 0 mg/liter. Bacterial inocula used for each level of inoculation were $1-5 \times 10^4$ cfu/100 µl. The assays were performed in microliter wells at 35° C. for 18 hours.

Results of the experiment were summarized in Table VI. The bacteria are defined as "resistant" to cephalothin if the organism has an MIC of $\geq 32$ µg/ml, as "intermediate resistant" if the MIC is 16 µg/ml, and as "susceptible" if the MIC is 8 µg/ml as determined by the standard Muller Hinton broth (Manual of Clinical Microbiology, $6^{th}$ ed. 1995; ASM Press). Results of this experiment indicated that *E. coli, K. pneumoniae*, and *P. mirabilis* were susceptible, and *E. cloacae* was resistant to cephalothin as determined by the standard Muller Hinton broth and an antimicrobial susceptibility interpretation medium of this invention (CR30).

TABLE VI

| cephalothin | E. coli | | K. pneumoniae | | E. cloacae | | P. mirabilis | |
|---|---|---|---|---|---|---|---|---|
| | MHB | CR30M | MHB | CR30M | MHB | CR30M | MHB | CR30M |
| 0 | + | + | + | + | + | + | + | + |
| 128 | − | − | − | − | + | + | − | − |
| 64 | − | − | − | − | + | + | − | − |
| 32 | − | − | − | − | + | + | − | − |
| 16 | − | − | − | − | + | + | − | − |
| 8 | + | + | − | − | + | + | − | − |
| 4 | + | + | − | − | + | + | − | − |
| 2 | + | + | − | + | + | + | − | − |

Example 6

In a presently preferred embodiment, this invention comprises a device having a series of 5 test wells. Each well comprises a specific medium coupled with a fluorogenic enzyme substrate for the detection of target bacteria and their respective antibiotic resistance patterns. The wells produce a fluorescent signal when bacteria grow in them.

The wells were termed a total viable bacteria "TVB" well, a primary gram negative urinary tract infection organisms "UTI" well, and individual wells which contain an antimicrobial susceptibility media with an antibiotic amoxicillin "AMO", clavulanic acid/amoxicillin (Clavamox®) "AMC", or enrofloxacin (Baytril®) "ENR".

The total viable bacteria "TVB" well, when it fluoresces, indicates the presence of bacteria in the urine sample. The "UTI" well fluoresces when the common Gram-negative uropathogens (*E. coli, Klebsiella* or *Enterobacter* spp., and *P. mirabilis*) are present in the urine sample. The antimicrobial susceptibility media wells, e.g., the "AMO", "AMC", and "ENR" wells contain reagent mixtures with an antibiotic, amoxicillin, clavulanic acid/amoxicillin (AMC) (e.g., Clavamox®), and enrofloxacin (Baytril®) in each respective well.

If there is growth in the UTI well, and one or more of the antibiotic wells which do not fluoresce after the incubation period, this indicates that the uropathogens are susceptible to the antibiotic in the respective test well, i.e., the bacteria have not grown in this well. Such a result suggests that the test antibiotic is a preferred choice for treating the urinary tract infection. When the bacteria are resistant to the antibiotic, the wells fluoresce, suggesting that the test antibiotic is not a preferred choice for treatment.

Table VII presents typical data for use of a preferred embodiment.

TABLE VII

| Result Patterns[1] | | | | | | |
|---|---|---|---|---|---|---|
| TVB | UTI | AMO | AMC | ENR | Result Interpretation | Recommendation |
| − | − | − | − | − | No bacterial growth | |
| + | − | − | − | − | No common Gram (−) uropathogens[3] detected | Confirmation by a reference laboratory[2] |
| + | + | − | − | − | 1. Common Gram (−) uropathogens detected, 2. Uropathogens are susceptible to all three antibiotics | |
| + | + | + | − | − | 1. Common Gram (−) uropathogens detected, 2. Uropathogens are susceptible to Clavamox and enrofloxacin but are resistant to amoxicillin | |
| + | + | − | + | − | 1. Common Gram (−) uropathogens detected, 2. Uropathogens are susceptible to amoxacillin and enrofloxacin but are resistant to Clavamox | |
| + | + | − | − | + | 1. Common Gram (−) uropathogens detected, 2. Uropathogens are susceptible to amoxicillin and Clavamox but are resistant to enrofloxacin | |
| + | + | + | + | − | 1. Common Gram (−) uropathogens detected, 2. Uropathogens are susceptible to enrofloxacin but are resistant to amoxicillin and Clavamox | |
| + | + | + | − | + | 1. Common Gram (−) uropathogens detected, 2. Uropathogens are suspectable to Clavamox but are resistant to amoxicillin and enrofloxacin | |

TABLE VII-continued

| Result Patterns[1] | | | | | | |
|---|---|---|---|---|---|---|
| TVB | UTI | AMO | AMC | ENR | Result Interpretation | Recommendation |
| + | + | − | + | + | 1. Common Gram (−) uropathogens detected, | |
| + | + | + | + | + | 1. Common Gram (−) uropathogens | Confirmation by |

1. If an atypical result pattern is obtained, it is recommended that the test device be sent to a reference laboratory for confirmation or a fresh urine sample be collected and analyzed by a reference laboratory.
2. If these result patterns are obtained, it is also recommended that the test device be sent to a reference laboratory for standard microbial identification and antimicrobial susceptibility assays.

In a preferred embodiment, one of the antimicrobial susceptibility media contained amoxicillin, the second contained a combination of amoxicillin and clavulanic acid, and the third contained enrofloxacin. By comparing the development of fluorescence between the wells, it was determined whether primary gram negative urinary pathogens were present and if so, their susceptibility to these antibiotics.

Example 7

Four urine samples were used to inoculate four different devices prepared as described in Example 6. A total of 303 feline and canine urine specimens were collected from the animals suspected of having urinary tract infection were tested with the "AMO" medium. A 50 μl aliquot of the urine specimen was added to 10 ml of sterile saline solution (0.85% NaCl solution). A 100 μl of the diluted urine specimens were added to the individual test wells in the urinary tract infection device; the device was then incubated at 35° C. for 24 hours.

For each device, after an incubation period of 18 hours, the wells were examined for the development of fluorescence and conclusions about the presence of primary urinary pathogens and their susceptibility to the antimicrobial agents employed were drawn.

In Sample 1, both the TVB well and the UTI well developed fluorescence while none of the antimicrobial agent wells did. These results indicate that primary gram negative uropathogens are present which are susceptible to all three antimicrobial agents. In this case, for example, the health care practitioner would preferably treat with the lowest cost alternative of the three medications.

Sample 2 exhibited fluorescence in the TVB well, the UTI well, the AMO, and AMC wells, but exhibited no fluorescence in the ENR well. These results indicate that primary gram negative uropathogens are present which are resistant to both amoxicillin and clavulanic acid/amoxicillin (e.g., Clavamox), but are susceptible to enrofloxacin. The health care practitioner therefore would know in only 18 hours that the only effective treatment option of the three antimicrobial agents assayed is enrofloxacin. Time and money need not be wasted in treating with an antibiotic to which the organisms are not susceptible. This example also illustrates the further benefit that the development of new resistant strains of microorganisms is discouraged by exposing the organisms only to the minimum number of antibiotics possible, and only to those to which they are susceptible.

Sample 3 exhibited fluorescence in the TVB well, the UTI well, and all three antimicrobial agent wells. These results indicate a primary gram negative uropathogen resistant to all three assayed antibiotics. In this case the health care practitioner learns in only 18 hours that another course of therapy must be sought and that the urine sample should be sent to a laboratory for further confirmatory testing to obtain a full spectrum of antimicrobial susceptibility of the isolated urinary pathogen against other antibiotics or to perform the quantitative antimicrobial susceptibility tests. No time is wasted treating with antibiotics to which the organism is resistant and the quick realization of the presence of a resistant strain enables the patient to be treated more immediately with an effective course of therapy. Therefore, an additional benefit is that the further discomfort of the patient is minimized.

Finally, Sample 4 exhibited fluorescence only in the TVB well. Since the TVB well exhibits fluorescence the assay is valid. The fact that the UTI well did not exhibit fluorescence indicates that no primary gram negative uropathogens are present. This situation is consistent with a UTI caused by an organism which is not one of the primary uropathogens or a situation where there was contamination of the urinary sample. The health care practitioner could then obtain another urine sample or send the initial sample to a microbiology laboratory.

Example 8 (Ear Infection)

This example illustrates how a preferred embodiment of the invention is used to detect primary organisms associated with ear infections and to determine the susceptibility of such organisms to antimicrobial agents.

This embodiment comprises a total viable organisms "TVB" well and three primary ear infection organisms ("EIO") wells, one which contains a media capable of selectively sustaining the growth of gram positive primary ear infection organisms (e.g., *Staphylococcus* spp.) (EIO-S), another which contains a media capable of selectively sustaining the growth of primary gram negative ear infection organisms (e.g., *Pseudomonas* spp.) (EIO-P), and a third media capable of selectively sustaining the growth of *Candida* (CI), for the detection of yeast pathogens. There are also provided individual wells which contain antimicrobial susceptibility media. For the EIO-S and EIO-P associated wells, these antimicrobial agent wells contain the antibiotics gentamicin "GEN" and enrofloxacin (Baytril®) "ENR." For the CI associated wells, the antimicrobial agent wells contain Tresderm "TRE" and Odemax "ODE." Therefore, a total of ten wells are provided in this embodiment.

Fluorescence in the total viable organisms "TVB" control well indicates the presence of nonspecific bacteria and fungi in the sample. The EIO-S and EIO-P wells fluoresce when the common gram negative or gram positive pathogens associated with ear infections for which the media select (*Staphylococcus* spp. or *Pseudomonas* spp.), respectively, are present in the sample. The "CI" well fluoresces when yeast are present in the sample. The "GEN," "ENR," "TRE," and "ODE" wells exhibit fluorescence when organisms resistant to that antimicrobial agent are present in the sample and do not fluoresce when susceptible organisms are present since no growth has occurred.

For example, a sample is presented into each well and incubated for 18–24 hours. Fluorescence is exhibited in the TVO well, the EIO-S well and the GEN well. No fluorescence is exhibited in the EIO-P well or CI well or any of their associated antimicrobial agent wells. These results indicate the presence of a pathogen from the gram positive *Staphylococcus* spp. group which is susceptible to enrofloxacin but resistant to gentamicin.

Example 9 (Skin Infection)

In another preferred embodiment, the invention is used to detect primary organisms associated with skin infections and to determine the susceptibility of the organisms to antimicrobial agents.

This embodiment comprises a total viable organisms "TVB" well, a primary skin infection organisms ("SIO") well, and individual wells which contain an antimicrobial susceptibility media with an antibiotic Cephalothin "CR30," enrofloxacin (Baytril®) "ENR," and keflex "KEF".

Fluorescence in the total viable organisms "TVB" well indicates the presence of bacteria in the sample from the skin. The "SIO" well fluoresces when common pathogens associated with skin infections are present in the sample. The "CR30," "ENR," and "KEF" wells contain antimicrobial susceptibility media with an antibiotic cephalothin, enrofloxacin (Baytril®), or keflex in their wells, respectively.

If there is growth in the TVB, or, TVB and SIO wells, other wells which do not fluoresce after the incubation period indicate that bacteria have not grown in that well and thus the pathogens present are susceptible to the antibiotic in that respective test well. Therefore, that antibiotic would be indicated as a potential course of treatment for the skin infection, whereas fluorescence in a well indicates that the pathogens are growing despite the presence of the antibiotic and that the organism is resistant to this antibiotic.

For example, each well is inoculated with an aliquot of a biological sample from a skin infection. After an incubation period of 18 hours, the wells are examined for the development of fluorescence. If fluorescence is found in the TVB well, the SIO well, and the CR30 well, this indicates that primary skin infection organisms are present which are resistant to cephalothin. Therefore, the health care practitioner is free to choose the lowest cost alternative between enrofloxacin and keflex. Similarly, if fluorescence is found in the TVB well, the SIO well, and both the CR30 and KEF wells, this indicates primary gram negative skin infection organisms are present which are resistant to both cephalothin and keflex. The health care practitioner, therefore, learns in only 18 hours the resistance pattern of the infection-causing organisms and, in this case, knows that enrofloxacin will be an effective treatment option. Accordingly, no time is wasted treating with antibiotics to which the organism is resistant, and the rapid realization of the presence of a resistant strain enables the patient to be treated more immediately with an effective course of therapy. Thus, an additional benefit is that further discomfort of the patient is minimized.

Example 10 (General)

In other preferred embodiments the invention is used to determine the presence and susceptibility of organisms associated with many types of infections. These organisms can be any microorganisms including, but not limited to, bacteria, protists, and fungi. These embodiments comprise devices having a series of test wells. Each well comprises a specific medium coupled with a enzymatic means for achieving a sensible signal, such as a fluorogenic substrate, calorimetric substrate or a substrate that yields a change in a chemical parameter such as pH upon enzymatic change. The enzymatic means achieves detection of target organisms of the particular type of infection of interest and when such enzymatic means are included in an antimicrobial susceptibility media with the respective antibiotic resistance and susceptibility patterns generally associated with that type of infection. Such wells produce a sensible signal (e.g., fluorescent, calorimetric or chemical) when organisms grow in them.

These embodiments contain wells termed a total viable organisms "TVB" well, a primary pathogenic organisms ("PPO") well, and individual wells which contain an antimicrobial susceptibility media with antimicrobial agents generally associated with the treatment of such infections and the resistance patterns particular to the subject organisms. These antimicrobial agents can be chosen strictly for reasons associated with effective treatment, to investigate more economical treatment options, for reasons associated with avoiding the development of resistant strains of organisms, or for reasons chosen to serve any value.

Color change will be discussed as a preferred sensible signal. Color change in the total viable organisms "TVB" control well indicates the presence of microorganisms in the sample. The "PPO" well changes color when common pathogens associated with the particular type of infection are present in the sample. Selective media for the PPO will be prepared to detect the pathogens of the particular type of infection in accordance with techniques known in the art. The antimicrobial agent wells which change color indicate that target organisms are present in the sample which are resistant to the antimicrobial agent present in the well. Wells which do not change color indicate that the organisms are susceptible to the antimicrobial agent present in the well. Therefore, the health care practitioner can tailor the treatment of the infection with important and accurate information obtained in only 18 hours. The treatment of infections can focus almost immediately on antimicrobial agents which are effective against the infecting organism. Patients obtain relief from the infection sooner because time need not be wasted treating with agents to which the organism are resistant. Moreover, the development of new resistant strains of infecting organisms is discouraged because infecting organisms are exposed to a minimum number of antimicrobial agents.

Therefore, the invention can acquire many embodiments and be broadly adapted to investigate the detection and treatment options for the particular types of organisms associate with various different infections.

Accordingly, the invention can comprise a device having any number of wells to enable the testing of a larger number of antibiotics and/or multiple samples. This would be particularly useful in achieving the goal of lowering the cost of treatment by testing not only the costly antibiotics and those with the greatest likelihood of success, but also cheaper drugs to which susceptibility may also be found. This also achieves the further goal of enabling health care practitioners to rely on newer, potent antibiotics only when absolutely necessary, thus discouraging the development of new resistant strains of bacteria to these new and valuable drugs.

CLOSING

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar to equivalent to those described herein can be used in the practice or testing of the invention, the preferred methods and materials are now described. All publications and documents mentioned herein are fully incorporated by reference.

What is claimed is:

1. A method of detecting the presence or urinary pathogens in a biological sample and of simultaneously determining the susceptibility of the urinary pathogens to antimicrobial agents, said method comprising:
   providing a multicompartment assay device comprising:
      at least one compartment comprising a medium capable of sustaining growth of total microbial organisms; at least one compartment comprising a uropathogenic specific medium; and, at least one compartment comprising an antimicrobial susceptibility interpretation medium;
   placing a portion of the biological sample respectively in said at least one compartment comprising a medium capable of sustaining growth of total microbial organisms; said at least one compartment comprising a uropathogenic specific medium; and, said at least one compartment comprising an antimicrobial susceptibility interpretation medium comprising an antimicrobial agent;
   whereby metabolism of a signal generating substrate and production of a detectable signal in said at least one compartment comprising a medium capable of sustaining growth of total microbial organisms indicates the presence of microbial organisms in the sample; metabolism of a signal generating substrate and production of a detectable signal in said at least one compartment comprising a uropathogenic specific medium indicates the presence of urinary pathogens in the sample; and metabolism of a signal generating substrate and production of a detectable signal in said at least one compartment comprising an antimicrobial susceptibility interpretation medium indicates that the organisms lack susceptibility to the antimicrobial agent comprised in said antimicrobial susceptibility interpretation medium; and
   examining the compartments to determine the presence of urinary pathogens in said biological sample and the susceptibility of said urinary pathogens to said antimicrobial agents.

2. The method of claim 1, wherein the biological fluid is urine.

3. The method of claim 2, wherein the urinary pathogens are primary gram negative urinary pathogens.

4. The method of claim 3 wherein the primary gram negative urinary pathogens comprise *Enterobacteriacae*.

5. The method of claim 3 wherein the primary gram negative urinary pathogens are selected from the group consisting of: *Escherichia coli, Klebsiella* spp., *Enterobacter* spp., *Proteus mirabilis Proteus vulgaris, Morganella morganii, Providencia retteri,* and *Acinetobacter* spp.

6. The method of claim 1 wherein the at least one antimicrobial susceptibility interpretation medium comprises amoxicillin, clavulanic acid/amoxicillin, or enrofloxacin.

7. The method of claim 1 wherein the signal generating substrate is fluorogenic or chromogenic.

8. A method of detecting the presence of urinary pathogens in a biological sample and of simultaneously determining the susceptibility of the urinary pathogens to antimicrobial agents, said method comprising:
   providing a multicompartment assay device comprising:
      at least one compartment comprising a medium capable of sustaining growth of total microbial organisms; at least one compartment comprising a uropathogenic specific medium comprising a methyl-umbelliferyl substrate; and, at least one compartment comprising an antimicrobial susceptibility interpretation medium;
   placing a portion of the biological sample respectively in said at least one compartment comprising a medium capable of sustaining growth of total microbial organisms; said at least one compartment comprising a uropathogenic specific medium comprising a methyl-umbelliferyl substrate; and, said at least one compartment comprising an antimicrobial susceptibility interpretation medium comprising an antimicrobial agent;
   whereby metabolism of a signal generating substrate and production of a detectable signal in said at least one compartment comprising a medium capable of sustaining growth of total microbial organisms indicates the presence of microbial organisms in the sample; metabolism of a methyl-umbelliferyl signal generating substrate and production of a detectable signal in said at least one compartment comprising a uropathogenic specific medium indicates the presence of urinary pathogens in the sample; and metabolism of a signal generating substrate and production of a detectable signal in said at least one compartment comprising an antimicrobial susceptibility interpretation medium indicates that the organisms lack susceptibility to the antimicrobial agent comprised in said antimicrobial susceptibility interpretation medium; and
   examining the compartments to determine the presence of urinary pathogens in said biological sample and the susceptibility of said urinary pathogens to said antimicrobial agents.

9. The method of claim 8, wherein the biological fluid is urine.

10. The method of claim 9, wherein the urinary pathogens are primary gram negative urinary pathogens.

11. The method of claim 10 wherein the primary gram negative urinary pathogens comprise *Enterobacteriacae*.

12. The method of claim 10 wherein the primary gram negative urinary pathogens are selected from the group consisting of: *Escherichia coli, Klebsiella* spp., *Enterobacter* spp., *Proteus mirabilis, Proteus vulgaris, Morganella morgani, Providencia retteri,* and *Acinetobacter* spp.

13. The method of claim 8 wherein the at least one antimicrobial susceptibility interpretation medium comprises amoxicillin, clavulanic acid/amoxicillin, or enrofloxacin.

14. A method of detecting the presence of urinary pathogens in a biological sample and of simultaneously determining the susceptibility of the urinary pathogens to antimicrobial agents, said method comprising:

providing a multicompartment assay device comprising:
at least one compartment comprising a medium capable of sustaining growth of total microbial organisms; at least one compartment comprising a uropathogenic specific medium comprising yeast extract; and, at least one compartment comprising an antimicrobial susceptibility interpretation medium;
placing a portion of the biological sample respectively in said at least one compartment comprising a medium capable of sustaining growth of total microbial organisms; said at least one compartment comprising a uropathogenic specific medium comprising yeast extract; and, said at least one compartment comprising an antimicrobial susceptibility interpretation medium comprising an antimicrobial agent:
whereby metabolism of a signal generating substrate and production of a detectable signal in said at least one compartment comprising a medium capable of sustaining growth of total microbial organisms indicates the presence of microbial organisms in the sample; metabolism of a signal generating substrate and production of a detectable signal in said at least one compartment comprising a uropathogenic specific medium comprising yeast extract indicates the presence of urinary pathogens in the sample; and metabolism of a signal generating substrate and production of a detectable signal in said at least one compartment comprising an antimicrobial susceptibility interpretation medium indicates that the organisms lack susceptibility to the antimicrobial agent comprised in said antimicrobial susceptibility interpretation medium; and
examining the compartments to determine the presence of urinary pathogens in said biological sample and the susceptibility of said urinary pathogens to said antimicrobial agents.

15. The method of claim 14, wherein the biological fluid is urine.

16. The method of claim 15, wherein the urinary pathogens are primary gram negative urinary pathogens.

17. The method of claim 16 wherein the primary gram negative urinary pathogens comprise *Enterobacteriacae*.

18. The method of claim 16 wherein the primary gram negative urinary pathogens are selected from the group consisting of: *Escherichia coli, Klebsiella* spp., *Enterobacter* spp., *Proteus mirabilis, Proteus vulgaris, Morganella morganii, Providencia retteri,* and *Acinetobacter* spp.

19. The method of claim 14 wherein the at least one antimicrobial susceptibility interpretation medium comprises amoxicillin, clavulanic acid/amoxicillin, or enrofloxacin.

* * * * *